(12) United States Patent
Manzo et al.

(10) Patent No.: US 7,824,401 B2
(45) Date of Patent: Nov. 2, 2010

(54) ROBOTIC TOOL WITH WRISTED MONOPOLAR ELECTROSURGICAL END EFFECTORS

(75) Inventors: Scott E Manzo, Shelton, CT (US); Justin Krom, Southington, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 989 days.

(21) Appl. No.: 11/094,639

(22) Filed: Mar. 30, 2005

(65) Prior Publication Data

US 2006/0079884 A1    Apr. 13, 2006

Related U.S. Application Data

(60) Provisional application No. 60/617,341, filed on Oct. 8, 2004.

(51) Int. Cl.
  *A61B 18/00* (2006.01)
  *A61B 18/04* (2006.01)
  *A61B 18/14* (2006.01)

(52) U.S. Cl. .............................. 606/41; 606/48; 606/50; 606/51; 606/52; 901/29

(58) Field of Classification Search .................... 606/41, 606/45, 48–52; 901/29
See application file for complete search history.

(56) References Cited

U.S. PATENT DOCUMENTS

| | | | |
|---|---|---|---|
| 5,184,601 A | 2/1993 | Putman | |
| 5,429,596 A | 7/1995 | Arias et al. | |
| 5,445,166 A | 8/1995 | Taylor | |
| 5,649,956 A | 7/1997 | Jensen et al. | |
| 5,792,135 A | 8/1998 | Madhani et al. | |
| 5,797,900 A | 8/1998 | Madhani et al. | |
| 5,800,423 A | 9/1998 | Jensen | |
| 5,807,378 A | 9/1998 | Jensen et al. | |
| 5,808,665 A | 9/1998 | Green | |
| 5,855,583 A | 1/1999 | Wang et al. | |

(Continued)

FOREIGN PATENT DOCUMENTS

WO    WO 99/50721 A1    10/1999

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

(Continued)

*Primary Examiner*—Roy D Gibson
*Assistant Examiner*—Kaitlyn E Helling

(57) ABSTRACT

A surgical instrument for use with a robotic surgical system is described. The instrument includes an elongate shaft having a proximal end and a distal end. An electrically live wrist member is disposed at the distal end of the shaft. An electrocautery end effector is mounted to the wrist member. An interface is disposed at the proximal end of the shaft. The interface is removably connectable to the robotic surgical system. A conductor extends from the interface to the end effector so as to deliver electrical energy to tissue engaged by the end effector. A tip cover is disposed over the wrist member so that electrical current can only be conducted to tissues through the exposed end effector (e.g., to promote blood coagulation during usage) and not to other parts of the patient's body.

26 Claims, 11 Drawing Sheets

U.S. PATENT DOCUMENTS

| | | | |
|---|---|---|---|
| 5,895,386 A * | 4/1999 | Odell et al. .................. 606/50 |
| 5,976,122 A | 11/1999 | Madhani et al. |
| 6,004,509 A | 12/1999 | Dey et al. |
| 6,102,909 A | 8/2000 | Chen et al. |
| 6,113,596 A | 9/2000 | Hooven et al. |
| 6,132,441 A | 10/2000 | Grace |
| 6,206,903 B1 | 3/2001 | Ramans |
| 6,246,200 B1 | 6/2001 | Blumenkranz et al. |
| 6,309,397 B1 | 10/2001 | Julian et al. |
| 6,312,435 B1 | 11/2001 | Wallace et al. |
| 6,331,181 B1 | 12/2001 | Tierney et al. |
| 6,364,888 B1 | 4/2002 | Neimeyer |
| 6,406,476 B1 * | 6/2002 | Kirwani et al. .................. 606/50 |
| 6,419,675 B1 * | 7/2002 | Gallo, Sr. ..................... 606/46 |
| 6,424,885 B1 | 7/2002 | Niemeyer et al. |
| 6,436,107 B1 | 8/2002 | Wang et al. |
| 6,464,701 B1 | 10/2002 | Hooven et al. |
| 6,488,680 B1 * | 12/2002 | Francischelli et al. ......... 606/41 |
| 6,491,691 B1 | 12/2002 | Morley et al. |
| 6,676,669 B2 | 1/2004 | Charles et al. |
| 6,702,805 B1 | 3/2004 | Stuart |
| 6,714,839 B2 | 3/2004 | Salisbury, Jr. et al. |
| 6,720,988 B1 | 4/2004 | Gere et al. |
| 6,746,443 B1 | 6/2004 | Morley et al. |
| 6,758,843 B2 | 7/2004 | Jensen |
| 6,783,524 B2 | 8/2004 | Anderson et al. |
| 6,788,018 B1 | 9/2004 | Blumenkranz |
| 6,817,974 B2 | 11/2004 | Cooper et al. |
| 2002/0111621 A1 * | 8/2002 | Wallace et al. ................. 606/41 |
| 2002/0128632 A1 * | 9/2002 | Cucin ......................... 604/542 |
| 2002/0188293 A1 * | 12/2002 | Manzo ........................ 606/45 |
| 2003/0023285 A1 * | 1/2003 | Eggers et al. ................. 607/96 |
| 2004/0253079 A1 | 12/2004 | Sanchez |
| 2004/0267254 A1 | 12/2004 | Manzo et al. |

OTHER PUBLICATIONS

U.S. Appl. No. 09/399,457, filed Sep. 17, 1999.
U.S. Appl. No. 10/957,077, filed Sep. 30, 2004.
U.S. Appl. No. 11/043,688, filed Jan. 24, 2005.
U.S. Appl. No. 60/111,711, filed Dec. 8, 1998.
U.S. Appl. No. 60/111,713, filed Dec. 8, 1998.
U.S. Appl. No. 60/285,485, filed Apr. 19, 2001.
U.S. Appl. No. 60/431,636, filed Dec. 6, 2002.
U.S. Appl. No. 60/617,341, filed Oct. 8, 2004.

* cited by examiner

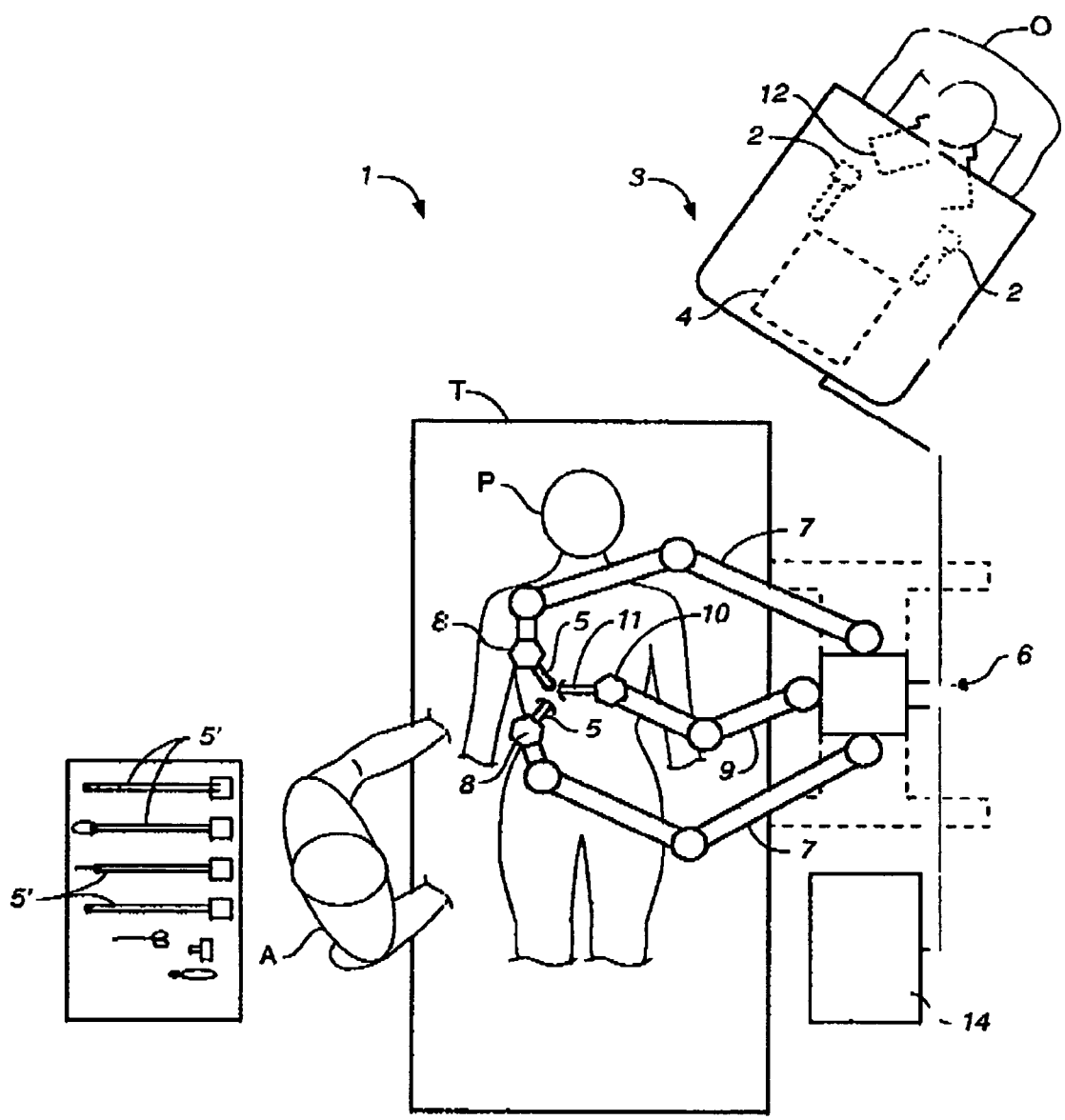
FIG._1

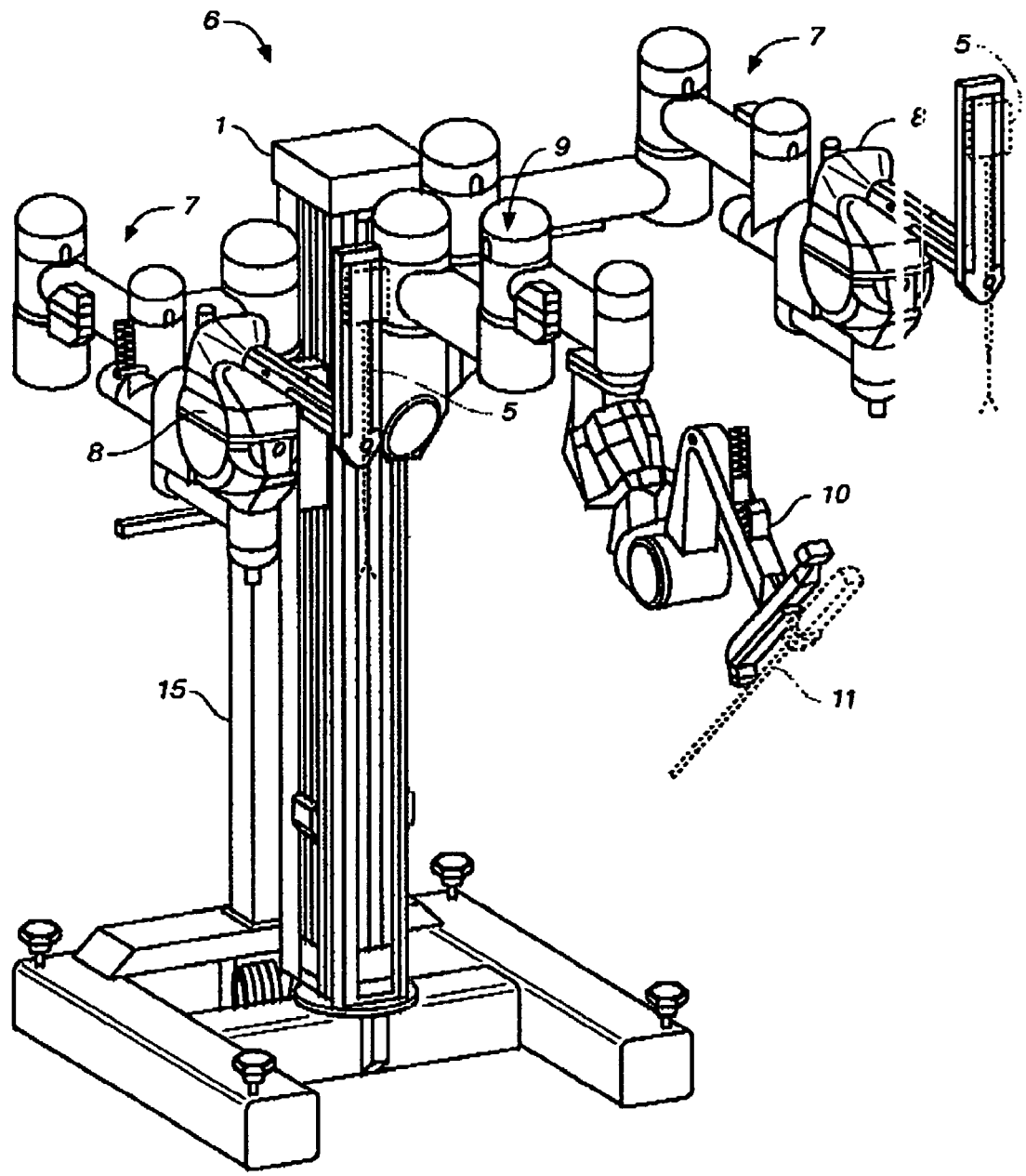
FIG._2

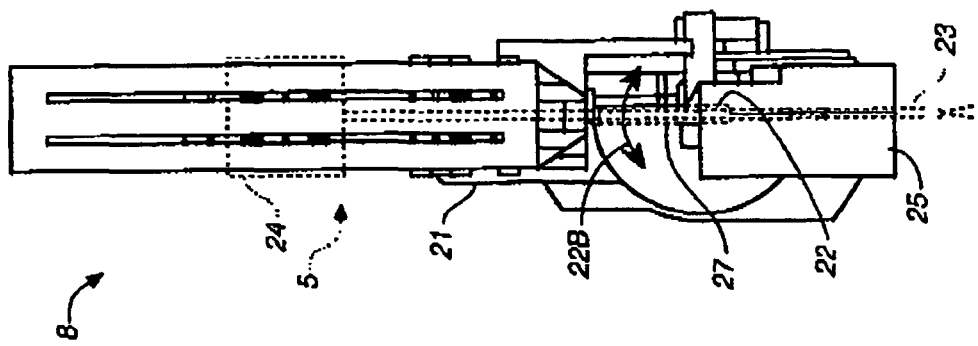
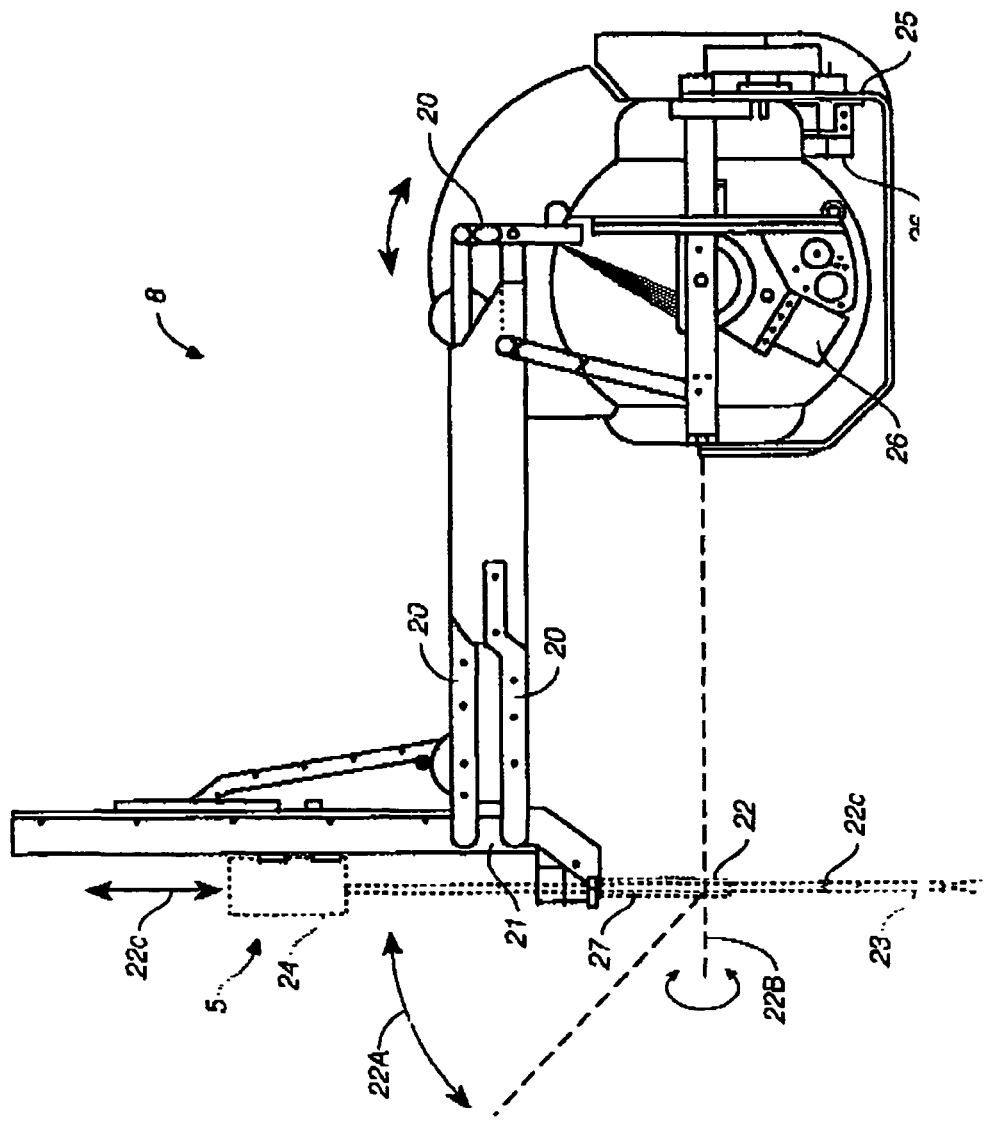
FIG._3B
FIG._3A

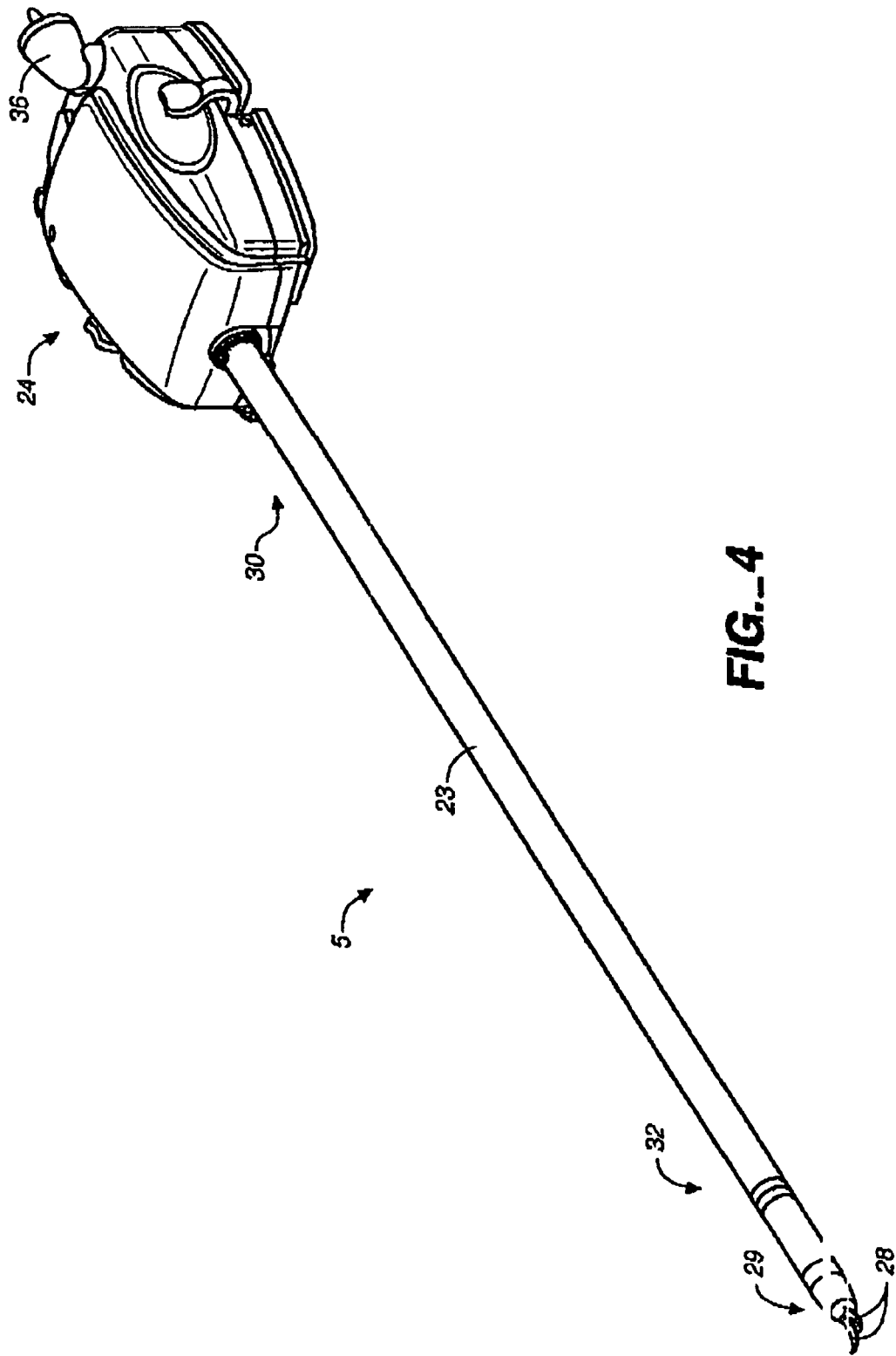
FIG._4

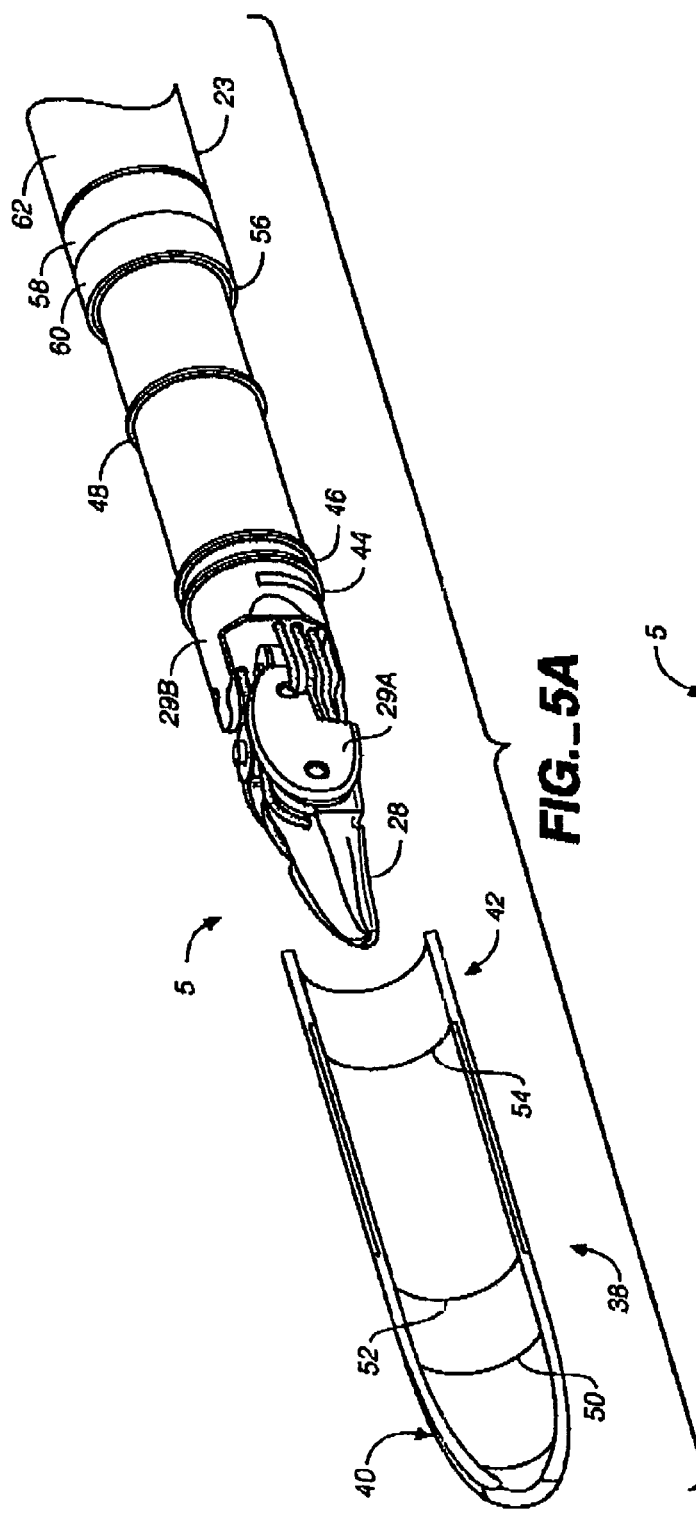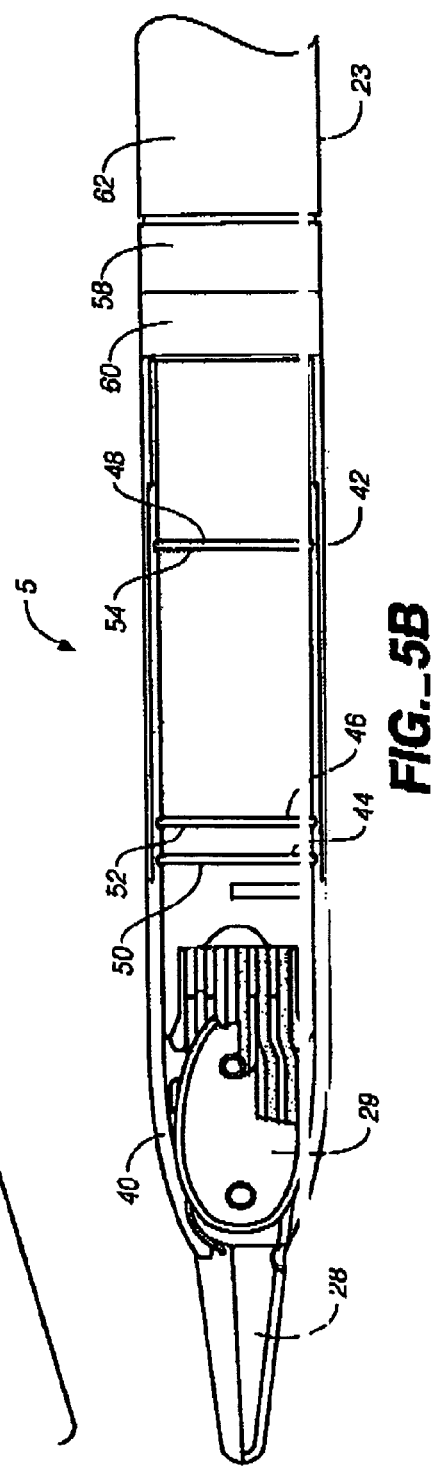

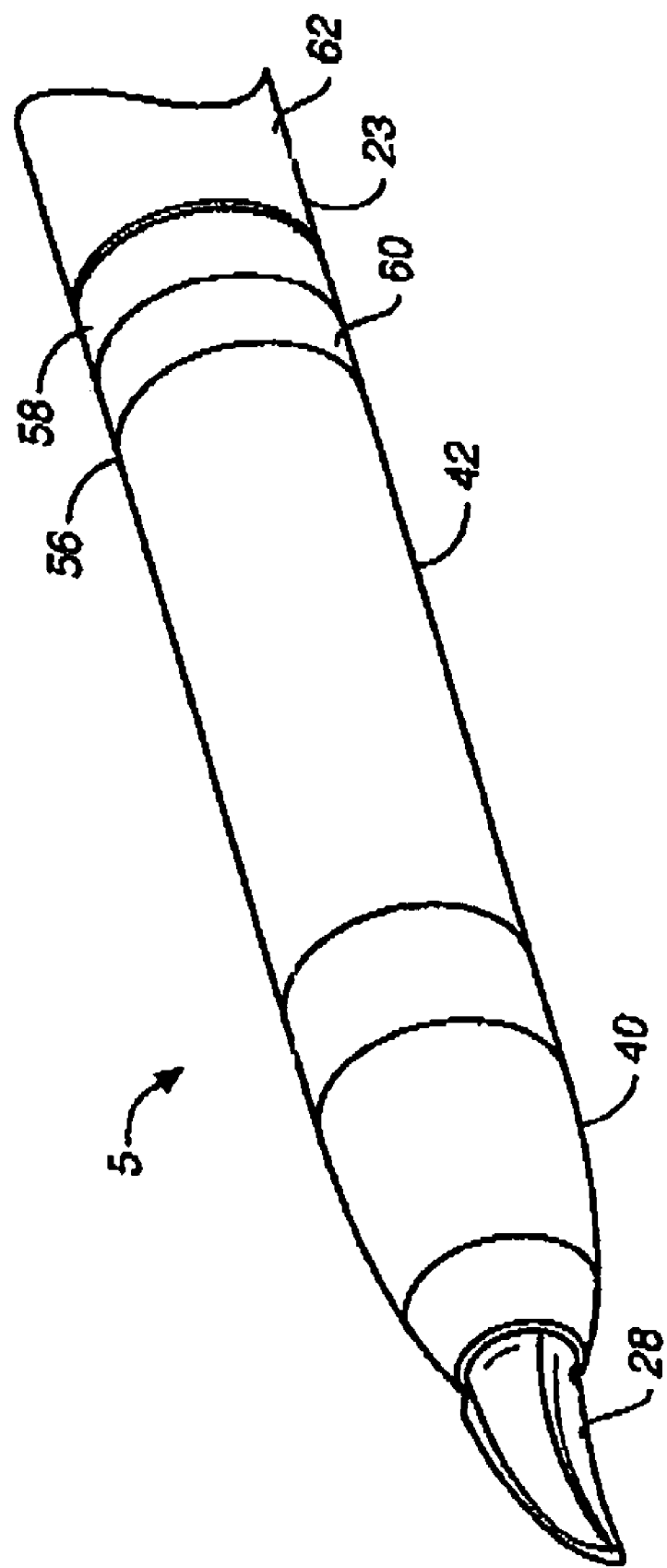
FIG._5C

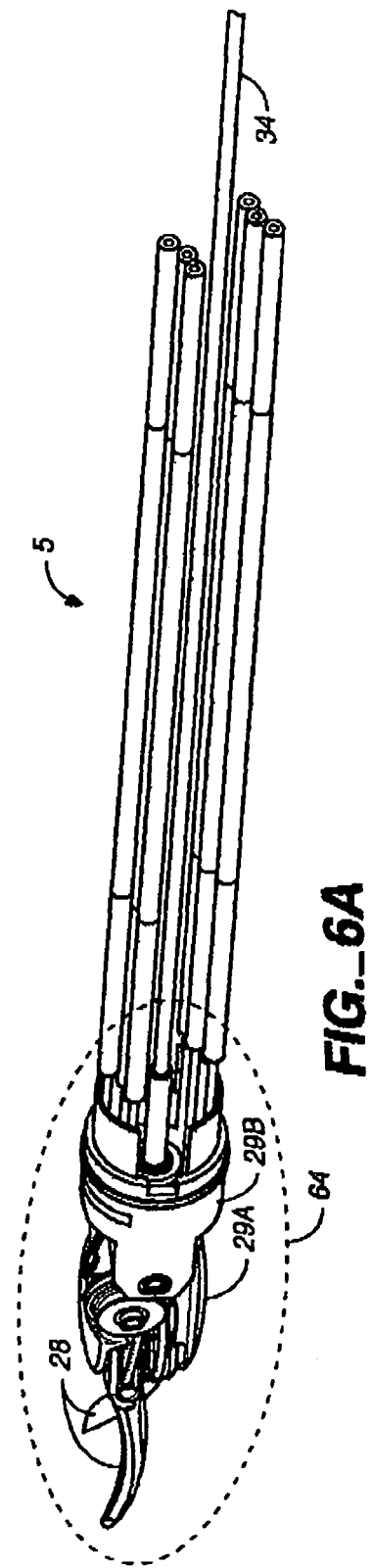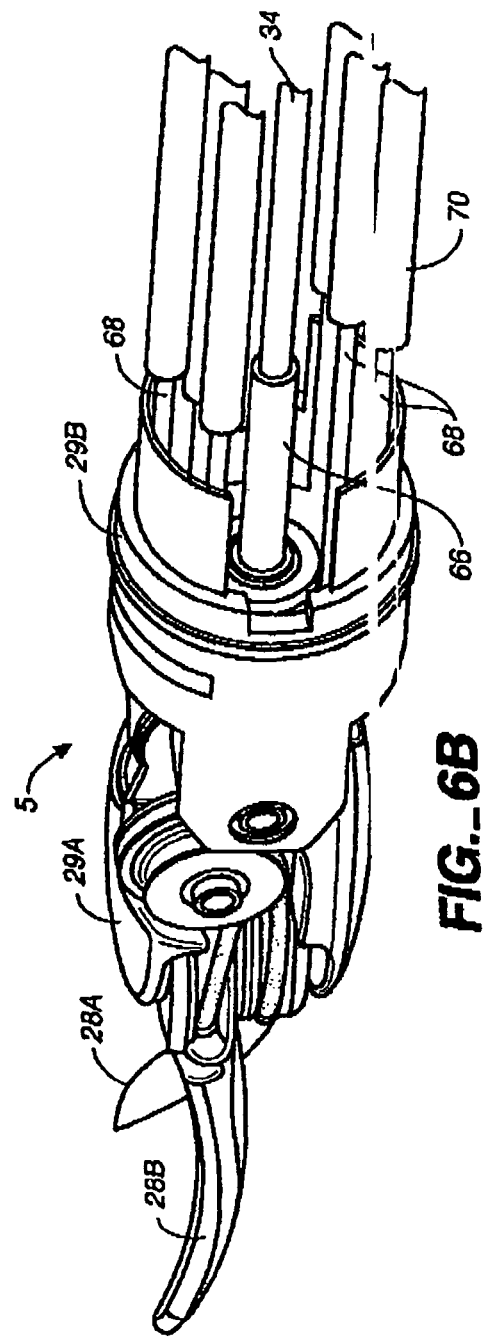
FIG._6A
FIG._6B

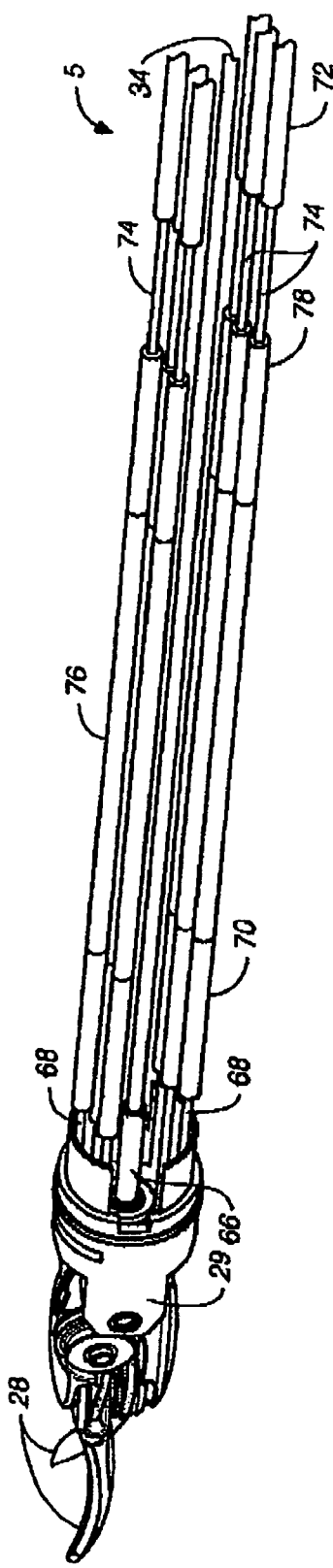
FIG._6C
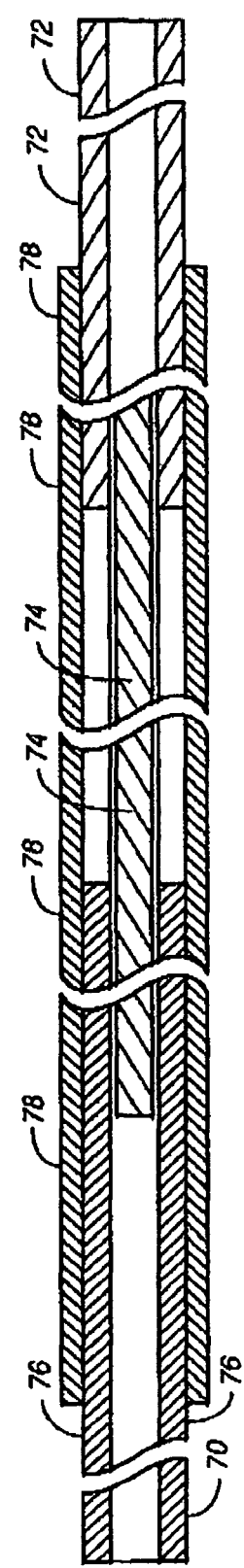
FIG._6D

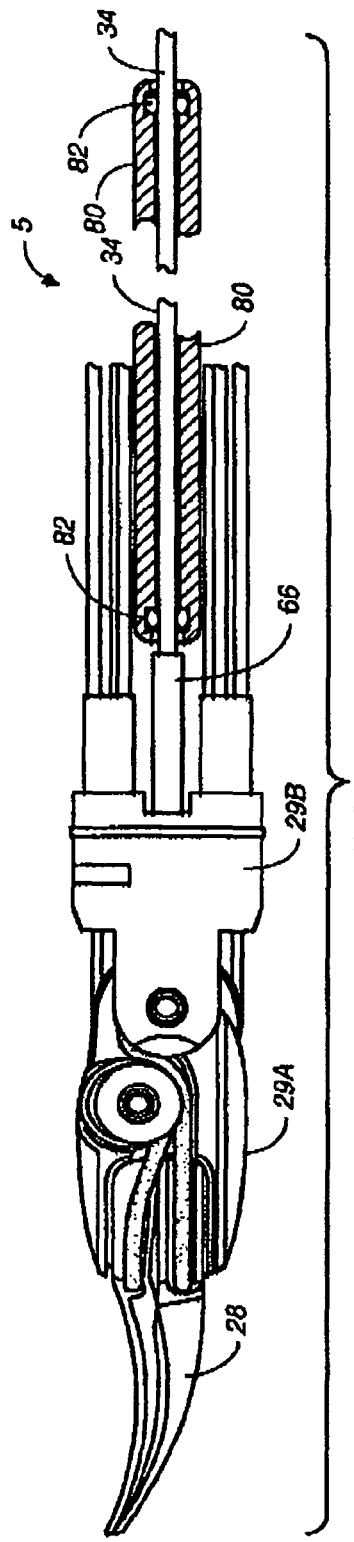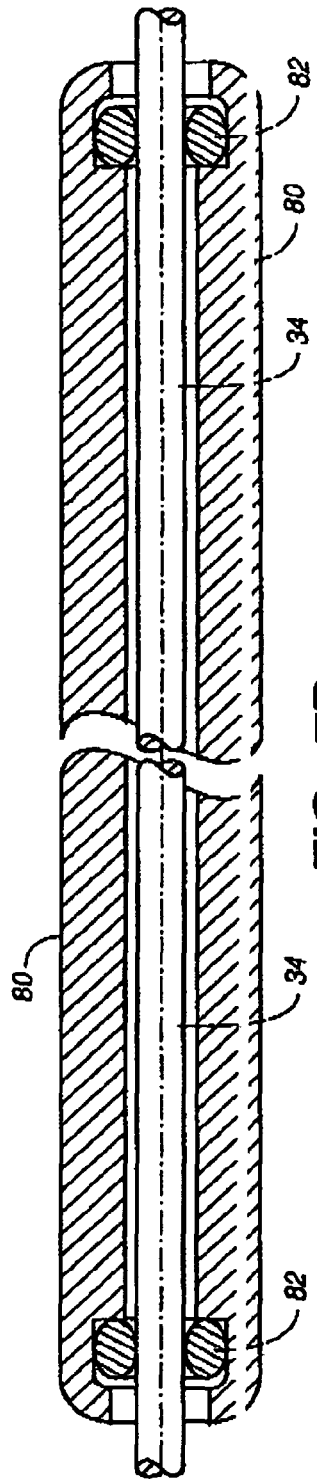

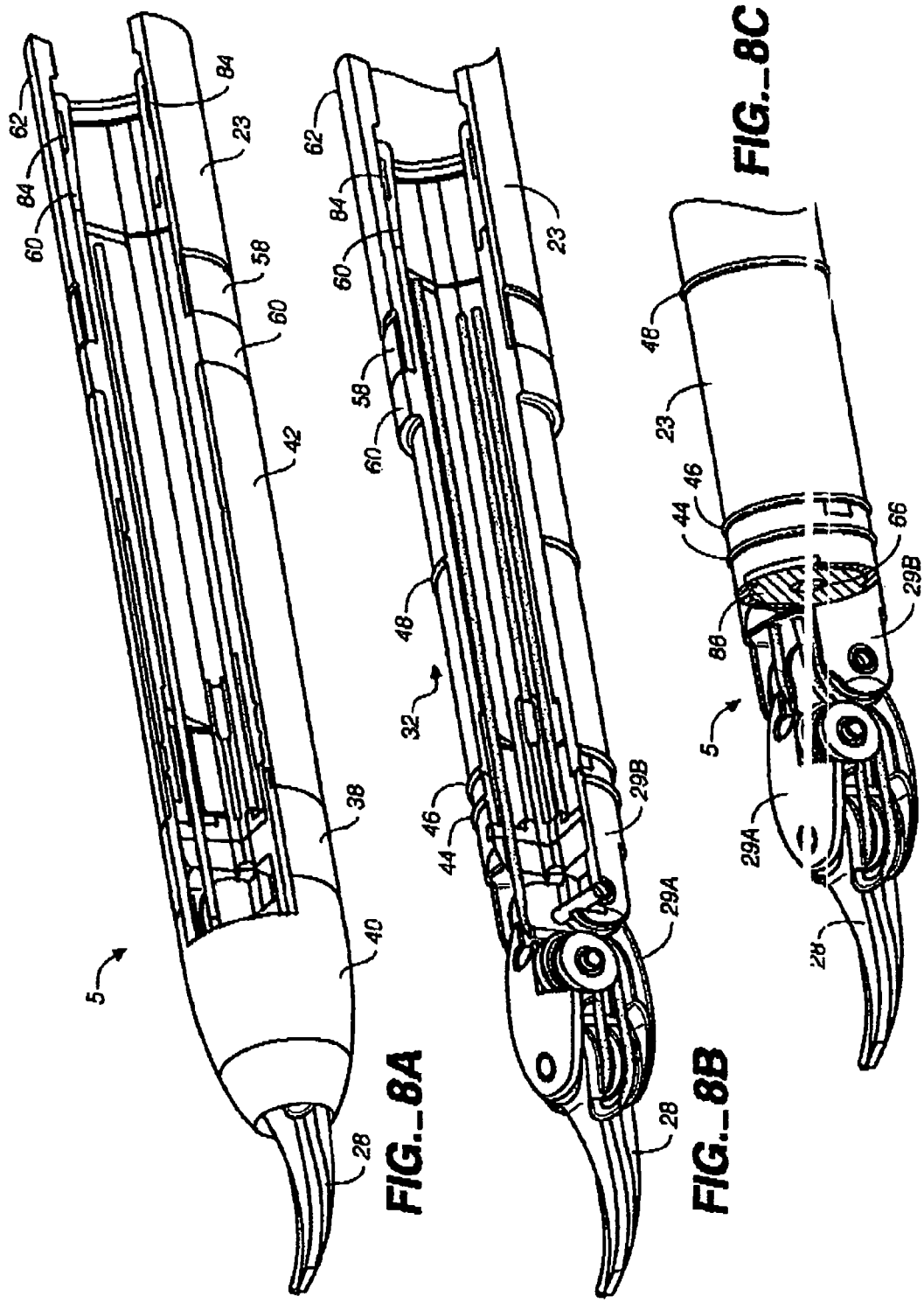

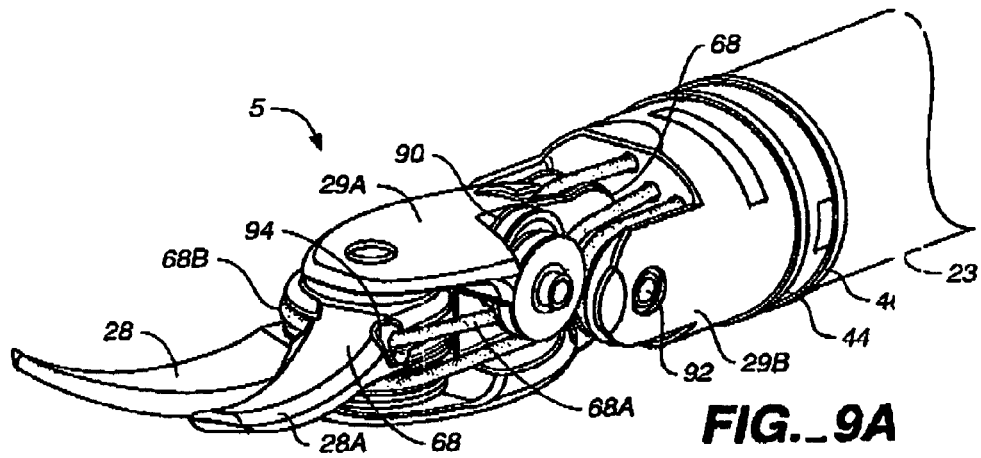
FIG._9A
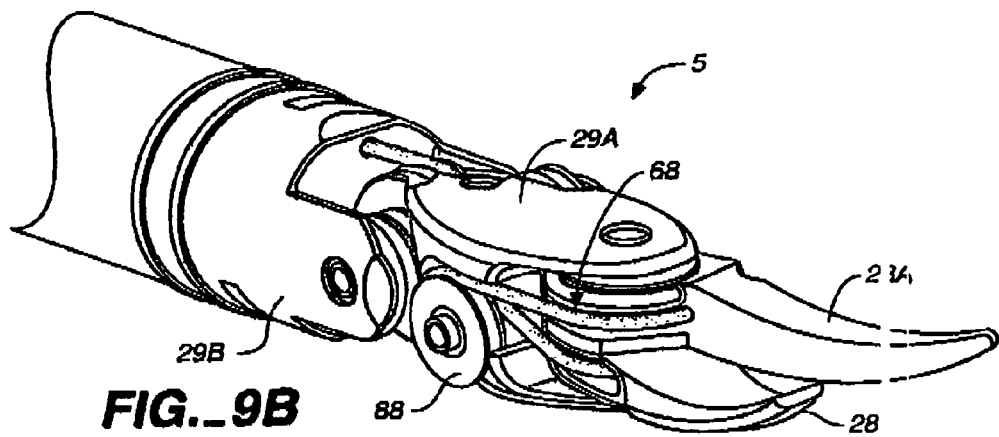
FIG._9B
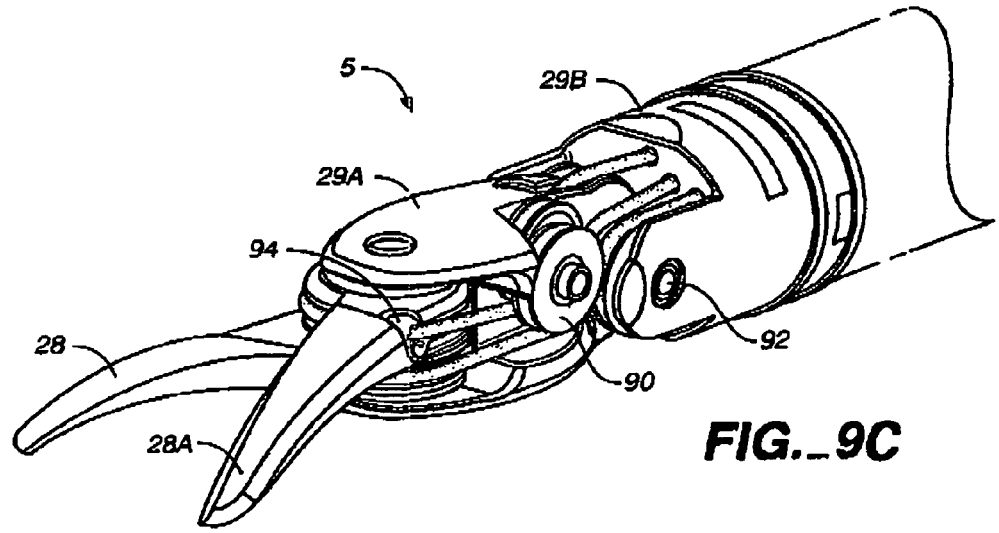
FIG._9C

ROBOTIC TOOL WITH WRISTED MONOPOLAR ELECTROSURGICAL END EFFECTORS

CROSS REFERENCES TO RELATED APPLICATIONS

This application claims the benefit of priority from U.S. Provisional Application No. 60/617,341, filed on Oct. 8, 2004, the full disclosure of which is incorporated herein by reference.

BACKGROUND OF THE INVENTION

The present invention is generally directed to surgical instruments or tools. In particular, the present invention relates to surgical instruments and systems that include wristed electrosurgical end effectors and methods of performing a surgical procedure. The surgical instruments can advantageously be used in robotically controlled minimally invasive surgical operations.

Minimally invasive medical techniques are intended to reduce the amount of extraneous tissue which is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard open surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system, such as those described in U.S. Pat. Nos. 6,364,888 and 6,424,885, the full disclosures of which are incorporated herein by reference. The control system typically includes at least one processor which relays input commands from the master controllers to the associated robotic arm and instrument assemblies and back from the instrument and arm assemblies to the associated master controllers in the case of, e.g., force feedback or the like. Mapping of the hand movements to the image displayed from the image capture device can help provide the surgeon with more control over movement of the surgical instruments. One example of a robotic surgical system is the DA VINCI® system available from Intuitive Surgical, Inc. of Sunnyvale, Calif.

The servo-mechanically driven linkage is sometimes referred to as a robotic surgical manipulator. Exemplary linkage arrangements for use as a robotic surgical manipulator during minimally invasive robotic surgery are described in U.S. patent application Ser. No. 10/957,077 and U.S. Pat. Nos. 6,758,843 and 5,800,423, the full disclosures of which are incorporated herein by reference. These linkages make use of a parallelogram arrangement to hold an instrument having a shaft. Such a manipulator structure can mechanically constrain movement of the instrument so that the instrument pivots about a point of spherical rotation positioned in space along the length of the rigid shaft. By aligning this pivot point with the incision point to the internal surgical site (for example, with a trocar or cannula at an abdominal wall during laparoscopic surgery), an end effector of the surgical instrument can be moved without imposing dangerous forces against the abdominal wall. Alternative manipulator structures are described, for example, in U.S. Pat. Nos. 6,702,805; 6,676,669; 5,855,583; 5,808,665; 5,445,166; and 5,184,601, the full disclosures of which are incorporated herein by reference.

A variety of structural arrangements can also be used to support and position the robotic surgical manipulator and the surgical instrument at the surgical site during robotic surgery. Supporting linkage mechanisms, sometimes referred to as set-up joint arms, are often used to position and align each manipulator with the respective incision point in a patient's body. The supporting linkage mechanism facilitates the alignment of a surgical manipulator with a desired surgical incision point. Exemplary supporting linkage mechanism are described in U.S. Pat. Nos. 6,246,200 and 6,788,018 and U.S. patent application Ser. No. 11/043,688, the full disclosures of which are incorporated herein by reference.

One type of end effector which is often advantageous for use with a robotic surgical system is an electrosurgical end effector. A typical electrosurgical treatment instrument is capable of treating tissue of an organism with the use of heat produced by electrical energy while cutting, shearing, grasping, or contacting the tissue. Such instruments are used to carry out treatments, such as incision, coagulation, and the like. Electrosurgical treatment and cutting instruments for both open surgery and manually performed endoscopic surgery have been described. For example, both monopolar and bipolar instruments are described in U.S. Pat. No. 6,102,909, the full disclosure of which is incorporated herein by reference. U.S. Pat. No. 6,132,441 and U.S. Publication No. 2004/0253079, describe robotically actuated surgical device and are also incorporated herein by reference. U.S. Publication Nos. 2004/0267254 and 2002/0188293 describe robotically controlled electrosurgical instruments and are assigned to the assignee of the present application and incorporated herein by reference. While such instrumentation has proven highly effective and advantageous, still further improvements would be desirable. In general, it would be desirable to provide instruments and systems that include wristed electrosurgical end effectors, such as cutting/shearing tools, which are preferably utilized in the course of robotic minimally invasive surgery.

BRIEF SUMMARY OF THE INVENTION

The present invention is generally related to surgical instruments or tools. In particular, the present invention relates to surgical instruments and systems that include wristed electrosurgical end effectors, such as cutting/shearing tools, and methods of performing a surgical procedure. The surgical instruments can advantageously be used in robotically controlled minimally invasive surgical operations. Such an instrument allows the advantages of electrosurgical treatment and minimally invasive robotic surgery to be combined, wherein the wrist member provides the additional advantage of maneuverability.

In a first aspect of the present invention, a surgical instrument for use with a robotic surgical system is provided. The instrument includes an elongate shaft having a proximal end and a distal end. An electrically live wrist member is disposed at the distal end of the shaft. An electrocautery end effector is mounted to the wrist member. An interface is disposed at the proximal end of the shaft. The interface is removably connectable to the robotic surgical system. A conductor extends from the interface to the end effector so as to deliver electrical energy to tissue engaged by the end effector. Surprisingly, an electrically live or conductive wrist member provides enhanced maneuverability while keeping an end effector length in tact.

The wrist member of the present invention is operational in a wet fluid filled environment, which is of particular benefit as pressurization within a patient body often drives fluid to enter the instrument. This is electrically acceptable as the wrist member and the end effector are at the same electrical potential. The wrist member may be formed from a variety of suitable conductive materials including metal (e.g., stainless steel) and like materials. The wrist member may be articulated to provide at least one degree of freedom, often two degrees of freedom, to the end effector relative to the shaft.

At least one insulation material is disposed over the wrist member so as to inhibit conduction of electrical current from the electrically live wrist member to the patient. For example, the insulation material acts as a barrier so as to prevent unwanted electrically-related patient burns at a location apart from the electrocautery end effector, particularly the area around the wrist member. In one embodiment, the insulation material comprises a cover, wherein the cover and shaft of the instrument have the same diameter. The cover may be removably disposable over the wrist member after use for a single use configuration. The overall outer diameter of the wrist member is kept small, for example, through the use of offset pulleys, offset clevis, and a tube extension. A compact or smaller diameter wrist member allows for a thicker cover insulation while still maintaining an overall diameter of the distal end of the instrument so that it may be received within a cannula. Under the present invention, the cover may also be a permanent one as well as a removably reusable (after sterilization) one.

A variety of other electrical isolation components are disposed in and around the instrument to prevent proximally-directed fluid into the shaft so that capacitive leakage of the instrument is minimized. Such components, as discussed herein, prevent electricity-related wear and tear, melting, and/or damage of parts of the instrument or unwanted patient burns at a location apart from the electrocautery end effector, particularly along a length of the shaft. For example, the instrument may include at least one seal disposed within the wrist member or the distal end of the shaft to prevent fluid from entering the shaft. The elongate shaft generally defines an internal longitudinally extending passage, wherein at least one actuation element extends within the passage from the interface for pivotally moving the wrist member or end effector. A tubing may extend along a length of the passage and over the at least one actuation element. In some instances, an electrical break along a length of the tubing is provided, using, for example, a VECTRAN® liquid crystal polymer (LCP) or non-conductive cable. The non-conductive cable preferably electrically insulates a proximal hypotube from a distal hypotube. Optionally, the instrument may further include at least one heat shrink insulation layer, preferably comprising fluorinated ethylene propylene, disposed over a length of the tubing or non-conductive cable to further reduce any capacitive leakage from the hypotubes. The heat shrink creates an electrical discontinuity between the proximal hypos and the distal hypos thru the full wrist ROM especially when proximal and distal hypos are close or potentially in contact. Additionally the insulation layer acts to keep the non-conductive cable dry by sealing to the hypotubes. If the non-conductive cable was wet an electrical current could conduct along the wetted fibers.

The end effector may comprise a variety of one or two finger elements formed from conductive materials, such as metal (e.g., stainless steel and the like. In an exemplary embodiment, the end effector comprises a pair of cooperative tissue shearing blades. The conductor electrically communicates with at least one blade so as to deliver electrical energy to tissue engaged by the blades. In other embodiments, the end effector may comprise a scalpel, blade, hook, spatula, probe, needle point, dissectors, graspers, movable jaws, and the like.

In another aspect of the present invention, an electrosurgical instrument is provided. The instrument includes an elongate shaft having a proximal end and a distal end. An electrically live wrist member is disposed at the distal end of the shaft. An electrocautery end effector is mounted to the wrist member. The wrist member provides at least one degree of freedom to the end effector relative to the shaft. A conductor electrically communicates with the wrist member and the end effector so as to deliver electrical energy to tissue engaged by the end effector.

In yet another aspect of the present invention, a robotic surgical system is provided. The system includes a robotic arm having an instrument holder. An electrosurgical instrument is detachably mountable on the instrument holder, the instrument having a proximal portion for engaging the instrument holder. An elongate shaft extends from the proximal portion to a distal end. An electrically live wrist member is disposed at the distal end of the shaft. An electrocautery end effector is mounted to the wrist member. A conductor extends from the proximal portion to the end effector so as to deliver electrical energy to tissue engaged by the end effector. The conductor is coupled to an electrical connector on the proximal portion. An electrosurgical generator is detachably connected to the connector of the proximal portion so as to transmit electrical current distally to the end effector.

In still another aspect of the present invention, a method of performing a robotic surgical procedure is provided. The method includes connecting a surgical instrument to a robotic surgical system. The surgical instrument includes an elongate shaft at a distal end of which a wrist member and end effector are disposed. The end effector, wrist member, and at least the distal end of the shaft are inserted through a minimally invasive incision in a patient body. Electrical energy is delivered to the end effector and wrist member, wherein the end effector engages tissue. The wrist member is operational in a fluid-filled environment. As described above, conduction of electrical current is inhibited from the wrist member or shaft to the patient or back of the surgical instrument by a variety of electrical isolation components. The method further includes articulating the wrist member so as to move the end effector in at least one degree of freedom relative to the shaft. In some embodiments, the method further comprises shearing the tissue cooperatively between a pair of blades of the end effector. Generally, delivering comprises transmitting radiofrequency energy in a monopolar fashion. The end effector, wrist member, and at least the distal end of the shaft are then retracted through the minimally invasive surgical incision.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

FIG. 1 is a schematic plane view of a portion of an operating theater illustrating a robotic surgical system, including a master surgeon console or workstation for inputting a surgical procedure and a robotic patient side cart for robotically moving surgical instruments having surgical end effectors at surgical sites.

FIG. 2 is a perspective view of the robotic patient side cart or stand, including positioning linkages which allow two patient side robotic manipulators and one endoscope camera robotic manipulator to be pre-configured.

FIGS. 3A and 3B are side and front views, respectively, of the linkage of the robotic manipulators of FIG. 2.

FIG. 4 is a perspective view of an exemplary articulated electrosurgical instrument constructed in accordance with the principles of the present invention for use in the system of FIG. 1.

FIGS. 5A through 5C are exploded perspective and cross-sectional views of the distal end of the electrosurgical instrument of FIG. 4.

FIGS. 6A through 6D are perspective and cross-sectional views of the electrosurgical instrument of FIG. 4 illustrating electrical and insulation components of the instrument.

FIGS. 7A and 7B are perspective and cross-sectional views of the electrosurgical instrument of FIG. 4 illustrating electrical insulation of the conductor.

FIGS. 8A through 8C are partial cross-sectional and perspective views of the distal end of the electrosurgical instrument of FIG. 4 illustrating further electrical isolation components of the instrument.

FIGS. 9A through 9C are perspective views of the distal end of the electrosurgical instrument of FIG. 4 illustrating actuation components of the instrument.

DETAILED DESCRIPTION OF THE INVENTION

FIGS. 1 through 3B illustrate a robotic surgical system 1 for performing minimally invasive robotic surgery, which is described in more detail in U.S. Pat. No. 6,246,200. An operator O (generally a surgeon) performs a minimally invasive surgical procedure on patient P lying on operating table T, the operator O manipulating one or more input devices or masters 2 at a surgeon's console 3. In response to the surgeon's inputs, a computer processor 4 of console 3 directs movement of endoscopic surgical instruments or tools 5, effecting servomechanical movement of the instruments via a robotic patient side system 6 (a cart-mounted system in this example).

Typically, patient side system or cart 6 includes at least three robotic manipulator arms. Two set-up joint arms or linkages 7 (mounted at the sides of cart 6 in this example) support and position servo-manipulators 8 which drive surgical tools 5; and one set-up joint arm or linkage 9 (mounted at the center of cart 6 in this example) supports and positions servo-manipulator 10 which controls the motion of an endoscope camera probe 11, which captures an image (preferably stereoscopic) of the internal surgical site.

The image of the internal surgical site is shown to the surgeon or operator O by a stereoscopic display viewer 12 in surgeon's console 3, and is simultaneously shown to assistant A by an assistant's display 14. Assistant A assists in pre-positioning the manipulator 8 and 10 relative to patient P using set-up linkage arms 7, 9, in swapping tools 5 in one or more of surgical manipulator 8 (and/or 10) for alternative surgical tools or instruments 5', in operating related non-robotic medical instruments and equipment, and the like.

In general terms, the arms or linkages 7, 9 comprise a positioning linkage or set-up arm portion of patient side system 6, typically remaining in a fixed configuration while tissue is manipulated, and the manipulators 8, 10 comprise a driven portion which is actively articulated under the direction of surgeon's console 3. The manipulators 8, 10 are primarily used for master/slave tissue manipulation, while the set-up arms 7, 9 are used for positioning and/or configuring the manipulators 8, 10 before use, when repositioning the patient, operating table, incision points, and the like.

For convenience in terminology, a manipulator 8 for actuating tissue affecting surgical tools is sometimes referred to as a PSM (patient side manipulator), and a manipulator 10 for controlling an image capture or data acquisition device, such as endoscope 11, is sometimes referred to as an ECM (endoscope-camera manipulator), it being noted that such telesurgical robotic manipulators may optionally actuate, maneuver and control a wide variety of instruments, tools and devices useful in surgery.

FIG. 2 illustrates a perspective view of the cart mounted telesurgical patient side system 6 of FIG. 1, including at least two PSM's 8 and one ECM 10. Cart system 6 includes a column 15 which in turn mounts three positioning linkages or set-up arms, including two PSM set-up arms 7, each supporting one of the PSM's 8, and one ECM set-up arm 9 supporting ECM 10. The PSM set-up arms 7 each have six degrees of freedom, and are mounted one on each side of centrally mounted ECM set-up arm 9. The ECM set-up arm 9 shown has less than six degrees of freedom, and ECM 10 may not include all of the tool actuation drive system provided for articulated surgical instruments, such as are typically included in PSM 8. Each PSM 8 releasably mounts surgical tool 5 (shown in dashed lines) and ECM 10 releasably mounts endoscope probe 11 (shown in dashed lines).

FIGS. 3A and 3B are side and front views, respectively, of the linkage of the robotic surgical manipulator or PSM 8 of FIG. 2, having a remote center mechanism. PSM 8 is one example of a manipulator which may be mounted and supported by a cart mount 6, ceiling mount, or floor/pedestal mount. In this example, the PSM 8 preferably includes a linkage arrangement 20 that constrains movement of tool interface housing 21 and mounted instrument or tool 5. More specifically, linkage 20 includes rigid links coupled together by rotational joints in a parallelogram arrangement so that housing 21 and tool 5 rotate around a point in space 22, as more fully described in issued U.S. Pat. No. 6,758,843.

The parallelogram arrangement of linkage 20 constrains rotation to pivoting, as indicated by arrow 22a in FIG. 3A, about an axis, sometimes called the pitch axis, which is perpendicular to the page in that illustration and which passes through pivot point 22. The links supporting the parallelogram linkage are pivotally mounted to set-up joint arms (7 in FIG. 2) so that tool 5 further rotates about an axis 22b (FIG.

3B), sometimes called the yaw axis. The pitch and yaw axes intersect at the remote center 22, which is aligned along a shaft 23 of tool 5. Tool 5 has still further driven degrees of freedom as supported by manipulator 8, including sliding motion of the tool along insertion axis 22c. Tool 5 includes proximal housing 24 which mounts to manipulator interface housing 21. Interface housing 21 both provides for motion of the tool 5 along axis 22c and serves to transfer actuator inputs to tool 5 from the end effector actuator servo-mechanisms of PSM 8.

In this example of a remote center system, the parallelogram arrangement 20 is coupled to tool 5 so as to mechanically constrain the tool shaft 23 to rotation about pivot point 22 as the servomechanism actuates tool motion according to the surgeon's control inputs. As tool 5 slides along axis 22c relative to manipulator 8, remote center 22 remains fixed relative to mounting base 25 (mounting point to set-up arm 7) of manipulator 8. Hence, the entire manipulator 8 is generally moved to re-position remote center 22. Linkage 20 of manipulator 8 is driven by a series of motors 26 (FIG. 3A). These motors actively move linkage 20 in response to commands from a processor (4 in FIG. 1). For endoscopic procedures, manipulator 8 will often include a cannula 27. Cannula 27, which may be releasably coupled to manipulator 8, supports tool 5, preferably allowing the tool to rotate and move axially through the central bore of the cannula 27.

FIG. 4 illustrates a perspective view of an exemplary articulated electrosurgical tool or instrument 5 constructed in accordance with the principles of the present invention that may be employed in the system of FIG. 1. The instrument 5 includes an elongate shaft 23 having a proximal end 30 and a distal end 32. An electrically live wrist member 29 is disposed at the distal end 32 of the shaft 23, as best shown in FIG. 5A. An electrocautery end effector 28 is mounted to the wrist member 29. An interface 24 is disposed at the proximal end 30 of the shaft 23. The interface 24 is removably connectable to the robotic surgical system. A conductor 34 extends from the interface 24 to the end effector 28 so as to deliver electrical energy to tissue engaged by the end effector 28, as best shown in FIG. 6A. It will be appreciated that the above depictions are for illustrative purposes only and do not necessarily reflect the actual shape, size, or dimensions of the articulated electrosurgical instrument 5. This applies to all depictions herein.

The interface 24 is removably connectable to the robotic surgical system for releasably mounting and interfacing instrument 5 to a manipulator (e.g., PSM 8 in FIGS. 1, 2, 3A, and 3B). The interface 24 transmits drive signals and/or motion input from the robotic surgical system so as to move the wrist member 29 or end effector 28 in at least one degree of freedom relative to the interface. Further, the interface 24 comprises an electrical connector 36 for connecting the conductor 34 to an external electrosurgical generator. The end-effectors 28 are capable of treating tissue of an organism with the use of heat produced by electrical energy, though any other suitable form of energy may be used, such as ultrasound, microwave, laser, or photoablative energy. Electrical energy may be supplied by a conventional electrosurgical generator, such as the model Force F2 Electrosurgical Generator and related models made by Valley Lab of Boulder, Colo. The surgeon may activate an input, such as a foot switch electrically connected to the electrosurgical generator, causing the generator to supply electrical energy through a power cord and the connector to the instrument. Preferably, the conductor 34 transmits radiofrequency energy in a monopolar fashion to the end effector 28. Monopolar devices are typically used in conjunction with a grounding pad wherein one pole of an electrosurgical generator is mounted to the instrument and other pole is mounted to the grounding pad. The electrical current in monopolar devices travels from the instrument through the patient's body to the grounding pad.

Referring now to FIGS. 5A through 5C, exploded perspective and cross-sectional views of the distal end of the electrosurgical instrument 5 of FIG. 4 are illustrated. The wrist member 29 comprises electrically live distal clevis 29A and proximal clevis 29B components. The wrist member 29 of the present invention is operational in a wet fluid filled environment, which is of particular benefit as pressurization within a patient body often drives fluid to enter the instrument. This is electrically acceptable as the wrist member 29 and the end effector 28 are at the same electrical potential. The wrist member 29 may be formed from a variety of medical grade conductive materials including metal (e.g., stainless steel) and like materials. The end effector 28 may comprise a variety of one or two finger elements also formed from similar conductive materials as the wrist member 29.

As shown in FIG. 5B, an insulator or wrist cover 38 is disposed over the wrist members 29A, 29B and a distal end 32 of the shaft 23 so as to inhibit conduction of electrical current from the electrically live wrist member 29 to the patient's tissues at undesired/unintended locations along electrosurgical tool 5 to cause patient injuries during use. Rather, wrist cover 38 is designed so that when it is disposed properly in place, electrical current can only be conducted to tissues through the exposed end effector 28, for example, to promote blood coagulation during usage (e.g., cutting, shearing, etc.) and not to other parts of the patient's body. In one embodiment, wrist cover 38 comprises a flexible distal end 40 formed from insulation material, such as silicone rubber, and a rigid proximal tube 42 formed from plastic materials. Wrist cover 38 fits snugly over the end effector 28 as discussed in more detail below and may allow for fluid to enter flexible distal end 40 during use due to insufflation pressure. However, fluids in and around flexible distal end 40 are electrically acceptable as the wrist member 29 and the end effector 28 are at the same electrical potential. The wrist cover 38 provides suitable flexibility to the wrist member 29 while still insulating the live member 29 from the patient. The insulation material may comprise a variety of medical grade materials that provide high dielectric strength as well as arc track and flame resistance. Preferably, the cover 38 is disposable so as to provide for a single use per surgical procedure. However, cover 38 may also be designed to be reusable following sterilization. Alternatively, cover 38 may also be designed to attach permanently to the wrist member 29.

As shown in FIGS. 5A and 5C, the plastic tube 42 allows the cover 38 to be simply installed over the instrument 5 by sliding movement until it abuts a stop shoulder 56 of the shaft 23. Plastic tube 42 also supports three seals 44, 46, 48 on a distal end of the instrument 5, as discussed in more detail below. Plastic tube 42 further mates with the seals 44, 46, 48 at points 50, 52, 54 respectively so that the cover 38 is sufficiently retained over the instrument 5 and does not inadvertently fall off (FIG. 5B). Alternately, plastic tube 42 could be retained over instrument 5 utilizing interlocking snap features. Seals 44, 46, and 48 also prevent liquid from entering into undesired compartments along the instrument shaft thereby causing undesired electrical conductions to the back end of the instrument shaft. Preferably, the plastic tube 42 and shaft 23 of the instrument 5 have the same diameter and may be formed from and/or coated with similar medical grade non-conductive plastic (e.g., ULTEM®) or composite materials so as to keep a back end of the instrument 5 insulated from the electrically live wrist member 29. A metal ring 58 may optionally be inserted so as to limit deflection between tubular arms 60, 62 of the shaft 23 under bending loads.

Referring now to FIGS. 6A through 6D, further perspective and cross-sectional views of the electrosurgical instrument 5 are illustrated, wherein the tip cover 38 and shaft main tube 23 have been omitted. As discussed above, section 64 denotes electrically live metal components 28, 29 of the instrument 5. The insulated cautery conductor 34 extending distally from the interface 24 is electrically connected to the metal proximal clevis 29B by crimp 66, as best seen in FIG. 6B, which in turn is connected to the end effector 28. The end-effector 28 may comprise a combined cutting, shearing, clamping, stapling, or grasping device or any other suitable electrosurgery end-effector. As depicted herein, the end effector 28 comprises a pair of cooperative tissue shearing blades 28A, 28B that deliver electrical energy to tissue engaged by the blades. As the tissue current is conducted through the tissue, the tissue temperature rises, ultimately causing desiccation, cutting, cauterization, and/or coagulation of the treatment tissue (i.e., blood vessels and the like). The electrosurgical treatment may further reduce bleeding of tissue by cauterizing tissue and coagulating blood, or achieve various other desired effects on the treatment tissue. Voltages may range up to at least 12,000V in some cases, with about 3000V being a typical value, e.g., for coagulation.

As illustrated in FIG. 6C, a variety of electrical isolation components are disposed in and around the instrument to minimize capacitive leakage and/or coupling effects. In particular, the elongate shaft 23 generally defines an internal longitudinally extending passage, wherein six actuation elements or cables 68 extend within the passage from the interface 24 for pivotally moving the wrist member 29 or end effector 28. Proximal and distal hypotubes 72, 70 may extend along a length of the passage and over each actuation element 68. The hypotubes 70, 72 may be formed from and/or coated with non-conductive plastic or composite materials so as to reduce capacitive coupling effects. In particular, the short distal hypotubes 70 reduce capacitive current leakage near the electrically live wrist member 29.

Electrical breaks in the form of VECTRAN® liquid crystal polymer (LCP) cables 74 electrically insulates proximal hypotubes 72 from distal hypotubes 70. Advantageously, the isolation provided by the cables 74 creates electrical discontinuity so as to prevent proximally directed current towards a back end of the instrument 5. Cables 74 can also be made from other materials including: PBO (Zylon®) Aramid Copolymers (Technora®), nylons, polyesters, polyethelyene, and others. The instrument 5 further includes two insulation layers 76, 78 disposed over a length of the tubing 70, 72 or cable 74 to further counteract any capacitive leakage. As shown in FIG. 6D, the first insulation layer 76 may be made from parylene or another material and the second insulation layer 78 may be made from fluorinated ethylene propylene heat shrink, which is disposed in part over the first insulation layer 76. The fluorinated ethylene propylene heat shrink also minimizes the possibility of the hypotubes 70, 72 of each cable 68 from crossing and/or from fluid bridging the cables 74. It will be appreciated that the insulation layers of the present invention are not limited to parylene and fluorinated ethylene propylene materials. For example, other suitable insulation materials may include any heat shrinkable fluoropolymer and like materials.

Referring now to FIGS. 7A and 7B, perspective and cross-sectional views of the electrosurgical surgical instrument 5 illustrate electrical insulation 80 extending within the passage of the shaft 23 and over the electrocautery energy supply conductor 34. A pair of o-rings 82 are disposed within proximal and distal ends of the insulation tube 80 and between the conductor 34 so as to further seal the conductor. Sealed electrical insulation 80, 82 of the cautery conductor 34 reduces capacitive current leakage and/or capacitive coupling effects. The sealed conductor insulation is further described in detail in U.S. Publication No. 2004/0167515, which is assigned to the assignee of the present application and incorporated herein by reference.

FIGS. 8A through 8C are partial cross-sectional and perspective views of the distal end of the electrosurgical instrument 5 illustrating further electrical isolation components. As best seen in FIGS. 8B and 8C, the instrument 5 may further include two seals 44, 86 disposed within the proximal wrist member 29B and an additional three spaced apart seals 46, 48, 84 on the distal end 32 of the shaft 23 to prevent fluid from entering the shaft. Seals to control the ingress of proximally directed fluid flow from the tip cover into the main tube reduces current capacitive coupling between the shaft and the patient as well as current conduction to the back end of the instrument. Seal 84 is disposed between tubular arms 60, 62 of the shaft 23 so as to break direct electrical coupling paths from the inner shaft 60 to the outer shaft 62. Seals 44, 46, 48, 84, 86 may comprise o-rings, silicone potting, Silicone over-molding, elastomer over-molding (in general), and the like. As shown in FIG. 8A, the tip cover 38 further mates with seals 44, 46, 48, wherein the tip cover 38 and shaft 23 aim to inhibit conduction of electrical current from the wrist member or shaft to the patient or back of the surgical instrument 5.

Referring now to FIGS. 9A through 9C, perspective views of the distal end of the electrosurgical instrument 5 illustrate components of the actuation drive system. As discussed above, six actuation elements or cables 68 extend within the passage from the interface 24 (FIG. 4) for pivotally moving the wrist member 29 or end effector 28. An articulated wrist mechanism 29 may provide up to two degrees of freedom of motion between end effector 28 and shaft 23, while the shaft 23 may be rotatable relative to proximal housing 24 so as to provide the end effector 28 with three substantially orientational degrees of freedom within the patient's body. Motors 26 (FIG. 3A) are coupled to tool 5 so as to rotate the tool about axis 22c, and may articulate the wrist 29 at the distal end of the tool 5 about at least one, and often two, degrees of freedom. Additionally, motors 26 can be used to actuate the articulatable end effector 28 of the tool, in this case for cutting and/or shearing tissues. Motors 26 may be coupled to at least some of the joints of tool 5 using cables, as more fully described in U.S. Pat. Nos. 5,792,135; 6,206,903; 6,331,181; 6,371,952; 6,394,998; 6,817,974; 6,676,684; 6,685,698; and U.S. patent application Ser. Nos. 10/839,727 and 10/839,805, the full disclosures of which are incorporated herein by reference. For example, cable 68A may be actuated to open the upper jaw 28A while cable 68B may be actuated to close the upper jaw 28A.

As shown in FIGS. 9A and 9B, the distal wrist member 29A may define at least two pulleys 88, 90 offset from a pitch axis 92 so as to minimize an overall outer diameter of the distal wrist member 29A. A compact wrist member 29A allows for a thicker tip cover 38 to be received while still maintaining an overall diameter of the distal end of the instrument 5 so that it may be received within the cannula 27 of the manipulator 8 (FIG. 3A). The proximal clevis 29B further comprises seals 44, 86 (FIG. 8C) as discussed above as well as a reduced outer diameter, thin flanges, and a reduced pivot pin length so as to accommodate the tip cover 38. As shown in FIG. 9C, a notch 94 has been added to the scissor blades 28 to minimize high monopolar energy concentrations to the tip cover 38 and to provide an additional retention groove for the tip cover 38. Further, the blades 28 may be hand-polished, electropolished, or coated with a coating, such as TiN coating, to minimize any tissue sticking.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Therefore, the above description should not be taken as limiting the scope of the invention which is defined by the appended claims.

What is claimed is:

1. A surgical instrument for use with a robotic surgical system, the instrument comprising:
   an elongate shaft having a proximal end and a distal end;
   an electrically conductive wrist member having proximal and distal devices disposed at the distal end of the shaft;
   an electrocautery end effector mounted to the wrist member;
   an interface disposed at the proximal end of the shaft, the interface removably connectable to the robotic surgical system;
   a conductor extending from the interface and terminating at the proximal clevis of the electrically conductive wrist member so that the wrist member is the electrical connection between the conductor and the end effector; and
   at least one insulation material disposed over the wrist member so as to inhibit conduction of electrical current from the electrically live wrist member except to tissue engaged by the end effector.

2. The instrument of claim 1, wherein the wrist member is operational in a fluid filled environment.

3. The instrument of claim 1, wherein the wrist member and the end effector are at the same electrical potential.

4. The instrument of claim 1, wherein the wrist member comprises metal material.

5. The instrument of claim 1, wherein the wrist member provides at least one degree of freedom to the end effector relative to the shaft.

6. The instrument of claim 1, wherein the wrist member provides at least two degrees of freedom to the end effector relative to the shaft.

7. The instrument of claim 1, wherein the wrist member has a small overall outer diameter to allow for insulation.

8. The instrument of claim 1, wherein the insulation material comprises a cover, the cover and shaft having the same diameter.

9. The instrument of claim 8, wherein the cover is removable from the wrist member.

10. The instrument of claim 1, wherein the elongate shaft defines an internal longitudinally extending passage, wherein at least one actuation element extends within the passage from the interface for pivotally moving the wrist member or end effector.

11. The instrument of claim 10, further comprising a tubing extending along a length of the passage and over the at least one actuation element.

12. The instrument of claim 11, further comprising an electrical break along a length of the tubing.

13. The instrument of claim 12, wherein the electrical break comprises a liquid crystal polymer cable.

14. The instrument of claim 11, further comprising at least one insulation layer of parylene or fluorinated ethylene propylene disposed over a length of the tubing.

15. The instrument of claim 13, further comprising at least one insulation layer of parylene or fluorinated ethylene propylene disposed over a length of the liquid crystal polymer cable.

16. The instrument of claim 1, further comprising at least one seal disposed within the wrist member or the distal end of the shaft.

17. The instrument of claim 1, wherein the end effector comprises a pair of cooperative tissue shearing blades, the conductor electrically communicating with at least one blade so as to deliver electrical energy to tissue engaged by the blades.

18. The instrument of claim 1, wherein the end effector comprises a scalpel, blade, hook, spatula, probe, needle point, dissectors, graspers, or movable jaws.

19. An electrosurgical instrument comprising:
    an elongate shaft having a proximal end and a distal end;
    an electrically conductive wrist member having proximal and distal devices disposed at the distal end of the shaft;
    an electrocautery end effector mounted to the wrist member, wherein the wrist member provides at least one degree of freedom to the end effector relative to the shaft;
    a conductor terminating at the proximal clevis of the electrically conductive wrist member so that the wrist member is the electrical connection between the conductor and the end effector; and
    at least one insulation material disposed over the wrist member so as to inhibit conduction of electrical current from the electrically live wrist member except to tissue engaged by the end effector.

20. A robotic surgical system comprising:
    a robotic arm having an instrument holder;
    an electrosurgical instrument detachably mountable on the instrument holder, the instrument having a proximal portion for engaging the instrument holder, an elongate shaft extending from the proximal portion to a distal end, an electrically conductive wrist member having proximal and distal devices disposed at the distal end of the shaft, an electrocautery end effector mounted to the wrist member, and a conductor terminating at the proximal clevis of the electrically conductive wrist member so that the wrist member is the electrical connection between the conductor and the end effector, the conductor coupled to an electrical connector on the proximal portion, at least one insulation material disposed over the wrist member so as to inhibit conduction of electrical current from the electrically live wrist member except to tissue engaged by the end effector; and
    an electro surgical generator detachably connected to the connector of the proximal portion so as to transmit electrical current distally to the end effector.

21. A method of performing a robotic surgical procedure, the method comprising:
    connecting a surgical instrument to a robotic surgical system, the surgical instrument having an elongate shaft at a distal end of which an electrically conductive wrist member and end effector are disposed, the wrist member having proximal and distal devices;
    inserting the end effector, wrist member, and at least the distal end of the shaft through a minimally invasive incision in a patient body;

delivering electrical energy to the wrist member through a conductor terminating at the proximal clevis of the electrically conductive wrist member so that the wrist member is the electrical connection between the conductor and the end effector;

engaging tissue with the end effector; and inhibiting conduction of electrical current from the wrist member except to the tissue engaged by the end effector.

22. The method of claim 21, further comprising operating the wrist member in a fluid-filled environment.

23. The method of claim 21, further comprising articulating the wrist member so as to move the end effector in at least one degree of freedom relative to the shaft.

24. The method of claim 21, further comprising shearing the tissue cooperatively between a pair of blades of the end effector.

25. The method of claim 21, wherein delivering comprises transmitting radiofrequency energy.

26. The method of claim 21, wherein electrical energy is delivered in monopolar operation.

* * * * *